US011458315B2

(12) United States Patent
Brehm et al.

(10) Patent No.: US 11,458,315 B2
(45) Date of Patent: Oct. 4, 2022

(54) COCHLEAR IMPLANT SYSTEMS AND METHODS EMPLOYING A MICROPHONE NEAR THE EAR WITH AN OFF-THE-EAR SOUND PROCESSOR

(71) Applicant: Advanced Bionics AG, Staefa (CH)

(72) Inventors: Andreas Benedikt Brehm, Santa Clarita, CA (US); James George Elcoate Smith, Santa Clarita, CA (US); Anthony J. Spahr, Newhall, CA (US)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 17/258,936

(22) PCT Filed: Jul. 29, 2018

(86) PCT No.: PCT/US2018/043314
§ 371 (c)(1),
(2) Date: Jan. 8, 2021

(87) PCT Pub. No.: WO2020/023011
PCT Pub. Date: Jan. 30, 2020

(65) Prior Publication Data
US 2021/0337326 A1 Oct. 28, 2021

(51) Int. Cl.
*A61N 1/36* (2006.01)
*H04R 25/00* (2006.01)
(Continued)

(52) U.S. Cl.
CPC ..... *A61N 1/36038* (2017.08); *A61N 1/36146* (2013.01); *A61N 1/37229* (2013.01);
(Continued)

(58) Field of Classification Search
CPC ............ A61N 1/36038; A61N 1/36146; A61N 1/37229; A61N 1/0541; A61N 1/375;
(Continued)

(56) References Cited

U.S. PATENT DOCUMENTS 5,824,022 A  10/1998  Zilberman et al.
7,599,508 B1  10/2009  Lynch et al.
(Continued)

FOREIGN PATENT DOCUMENTS

CN    102215796 A    10/2011
CN    102245262 A    11/2011
(Continued)

OTHER PUBLICATIONS

International Search Report and Written Opinion received in International Application No. PCT/US18/43314. dated Apr. 2019.
(Continued)

*Primary Examiner* — Catherine M Voorhees
(74) *Attorney, Agent, or Firm* — ALG Intellectual Property, LLC

(57) ABSTRACT

An exemplary cochlear implant system for use by a recipient includes a microphone assembly and an off-the-ear (OTE) sound processor communicatively coupled with the microphone assembly. The microphone assembly includes a microphone configured to capture an audio signal representative of sound presented to the recipient, and a retention device configured to hold the microphone in place near an entrance to an ear canal of an ear of the recipient. The OTE sound processor includes a housing configured to be worn on a head of the recipient at a location that is off the ear of the recipient, and electronic circuitry included within the housing. The electronic circuitry is configured to generate stimulation parameters that, when transmitted to a cochlear implant implanted within the recipient, direct the cochlear implant to apply electrical stimulation representative of the captured audio signal to the recipient. Corresponding systems and methods are also disclosed.

20 Claims, 11 Drawing Sheets

(51) Int. Cl.
*A61N 1/372* (2006.01)
*A61N 1/05* (2006.01)

(52) U.S. Cl.
CPC .......... H04R 25/554 (2013.01); *A61N 1/0541* (2013.01); *H04R 25/606* (2013.01); *H04R 2225/021* (2013.01)

(58) Field of Classification Search
CPC .............. A61N 1/36036; H04R 25/554; H04R 25/606; H04R 2225/021; H04R 25/556; H04R 2225/67; H04R 25/552; H04R 2225/61
See application file for complete search history.

(56) References Cited

U.S. PATENT DOCUMENTS

| | | | | | |
|---|---|---|---|---|---|
| 8,437,859 | B1* | 5/2013 | Haller | ................ | A61N 1/36038 607/55 |
| 2005/0209657 | A1* | 9/2005 | Chung | ................ | A61N 1/36038 607/57 |
| 2008/0002834 | A1 | 1/2008 | Hochmair | | |
| 2010/0046778 | A1* | 2/2010 | Crawford | ................ | H04R 25/00 381/322 |
| 2011/0116669 | A1 | 5/2011 | Karunasiri | | |
| 2013/0116747 | A1* | 5/2013 | Crawford | ............. | H04R 25/556 607/57 |
| 2014/0073842 | A1* | 3/2014 | Maier | .................. | H04R 25/606 607/57 |
| 2014/0233775 | A1 | 8/2014 | Hartley et al. | | |
| 2014/0330344 | A1* | 11/2014 | Mishra | ............... | A61N 1/36038 607/57 |
| 2016/0317810 | A1 | 11/2016 | Crawford et al. | | |
| 2017/0189694 | A1* | 7/2017 | Palmer | ............... | A61N 1/36038 |
| 2017/0251312 | A1 | 8/2017 | Crawford et al. | | |
| 2020/0206499 | A1* | 7/2020 | Carter | .................. | A61N 1/0541 |

FOREIGN PATENT DOCUMENTS

| | | |
|---|---|---|
| WO | 2003015470 | 2/2003 |
| WO | 2010056751 | 5/2010 |
| WO | 2010056768 | 5/2010 |
| WO | 2010056770 | 5/2010 |
| WO | 2013101088 | 7/2013 |
| WO | 2015012815 | 1/2015 |
| WO | 2016015744 | 2/2016 |

OTHER PUBLICATIONS

Office Action received in Chinese Application No. 201880095771.X with an International Filing dated Jul. 23, 2018.

* cited by examiner

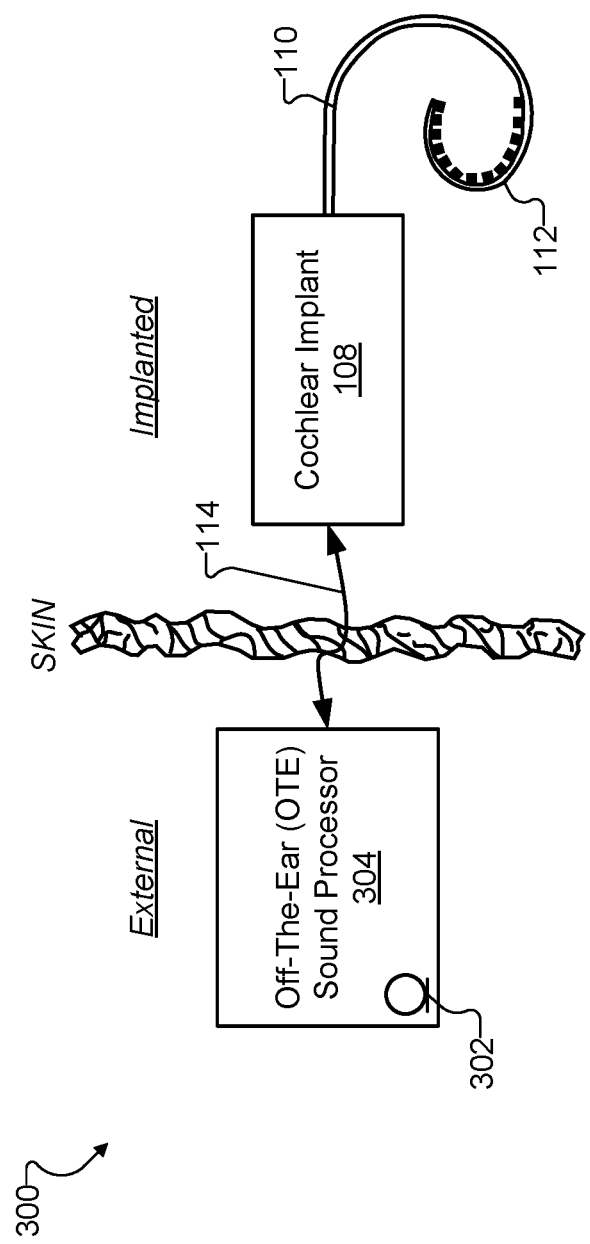

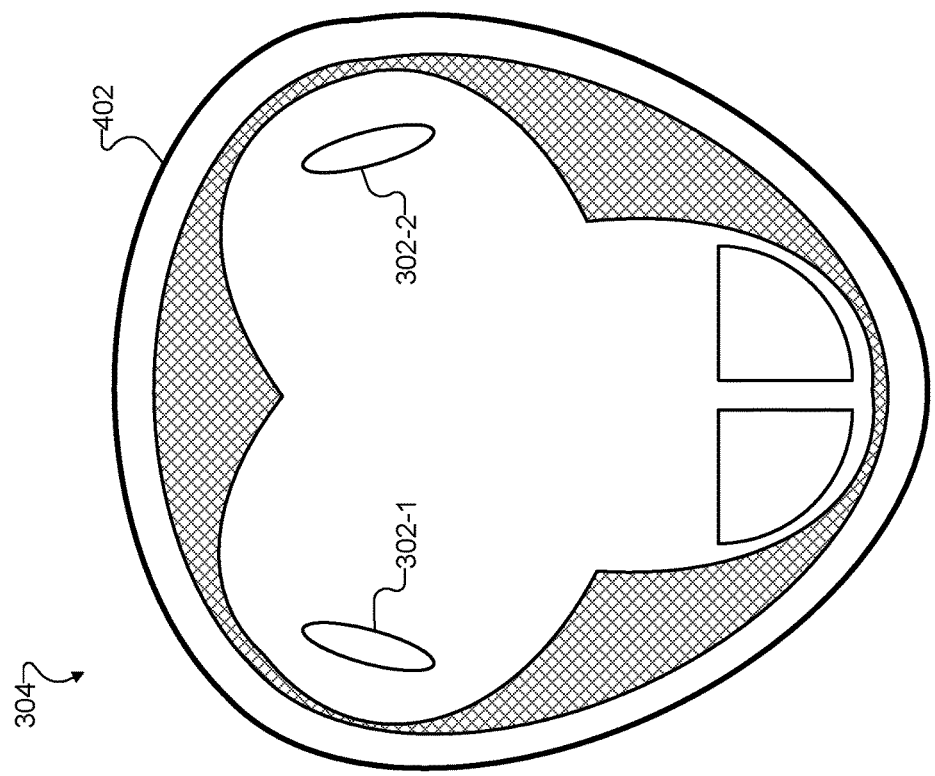
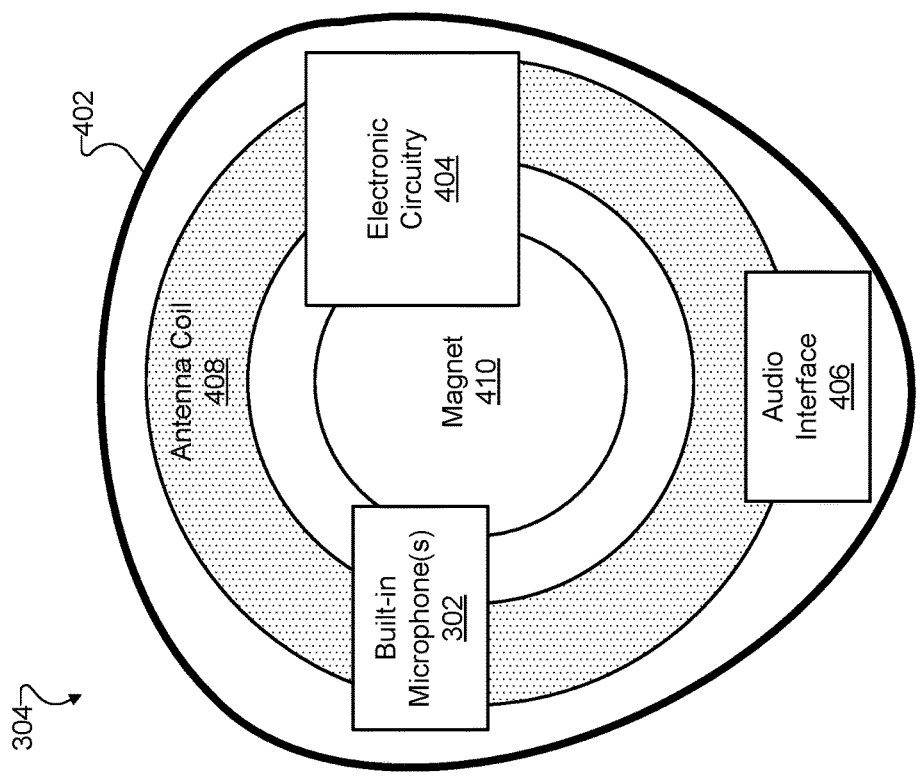

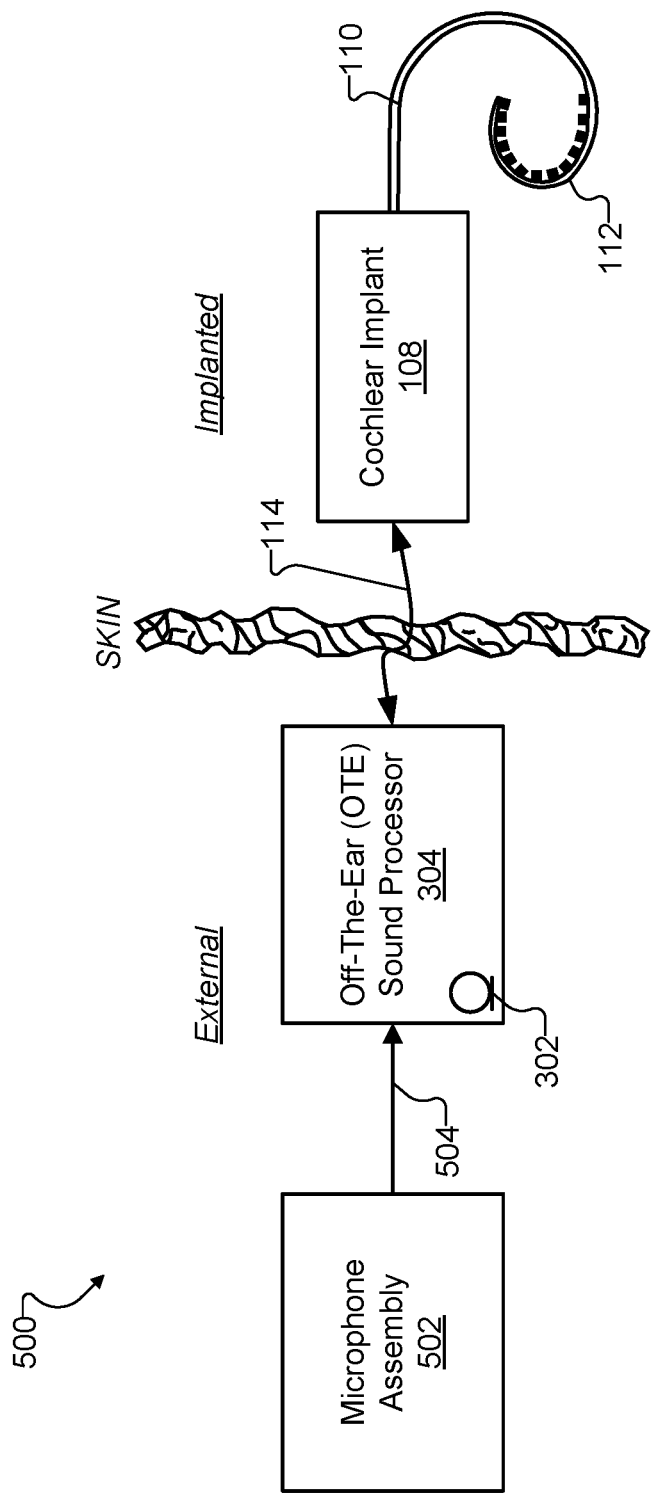

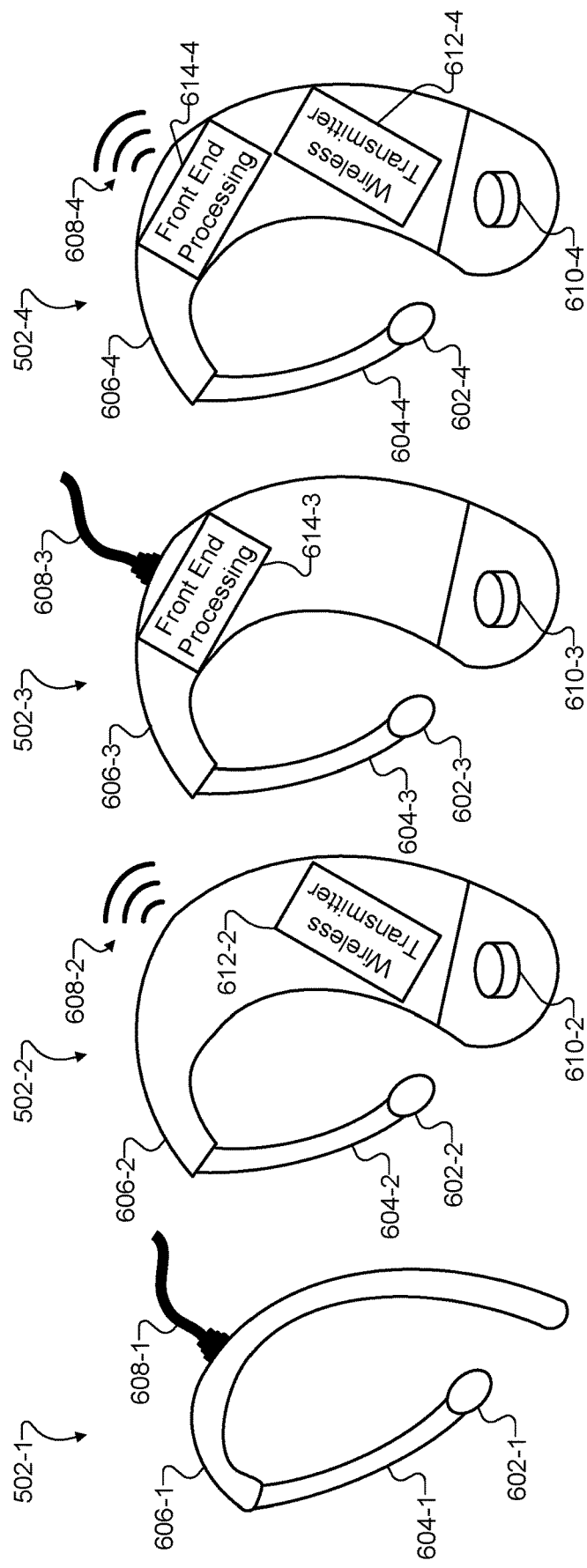

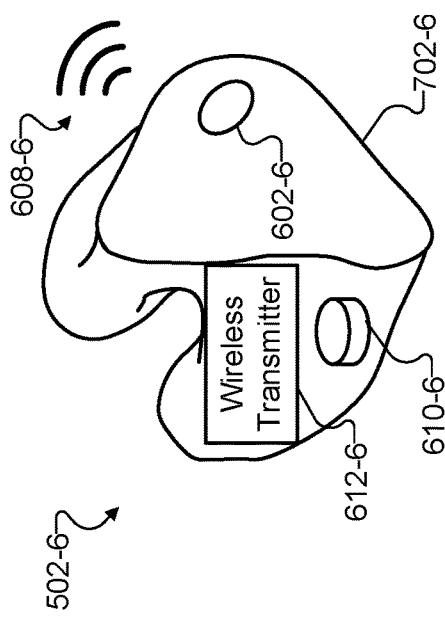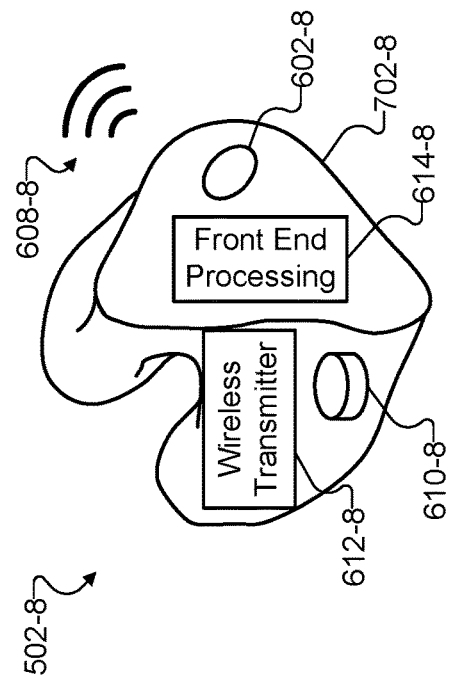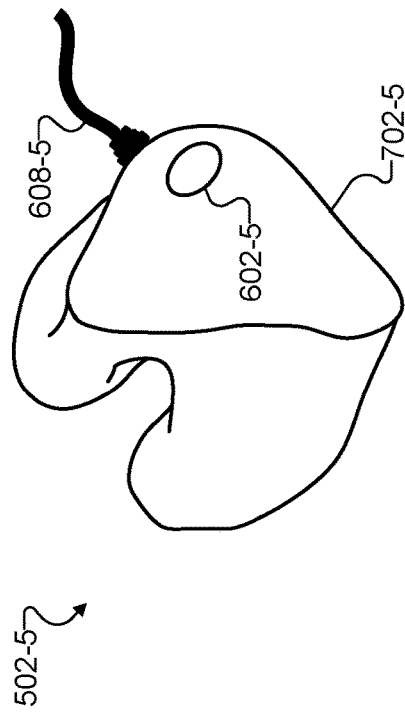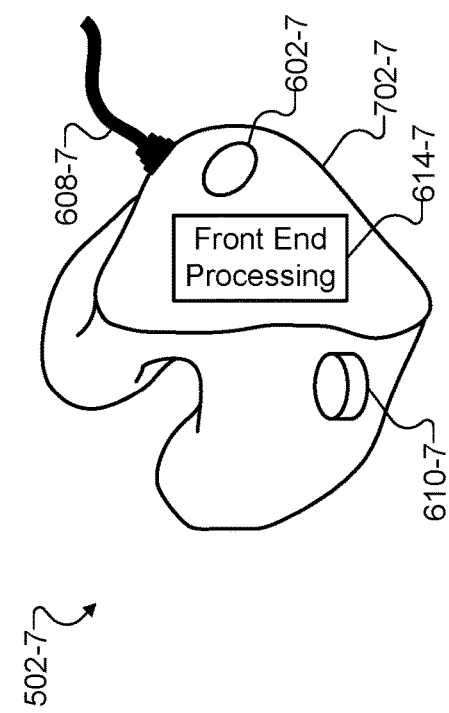

COCHLEAR IMPLANT SYSTEMS AND METHODS EMPLOYING A MICROPHONE NEAR THE EAR WITH AN OFF-THE-EAR SOUND PROCESSOR

BACKGROUND INFORMATION

Cochlear implant systems are used to provide, restore, and/or improve the sensation of hearing for cochlear implant recipients suffering from certain types of hearing loss. To this end, cochlear implant systems typically include: 1) a cochlear implant implanted within the recipient and configured to apply electrical stimulation to cochlear tissue of the recipient, 2) a headpiece that rests on the head over an implantation site of the cochlear implant to allow transcutaneous communication with the cochlear implant, and 3) a sound processor communicatively coupled with the cochlear implant by way of the headpiece and configured to provide power and stimulation parameters to direct the cochlear implant to apply the electrical stimulation to the recipient.

In different configurations, sound processors may be configured to be worn in different ways by the recipient. For example, certain sound processors are configured to be worn behind the ear of the recipient by attaching to the ear for support by way of an ear hook ("BTE sound processors"). Other sound processors are configured to be worn elsewhere, such as at an off-the-ear location on the head ("OTE sound processors") or off the head altogether and, for example, clipped onto clothing of the recipient or worn in a pocket ("body-worn sound processors").

BTE and body-worn sound processors are both associated with various disadvantages for certain recipients and/or situations that are remedied by OTE sound processors. For example, BTE sound processors may feel bulky to certain recipients (e.g., particularly pediatric recipients) and may be burdensome to carry on the ear all day. Moreover, BTE and body worn sound processors may be considered inconvenient or unsightly by certain recipients in certain situations (e.g., due to cabling between the sound processors and the headpiece, due to difficulty in waterproofing multiple components during activities such as showering or swimming, etc.). In spite of overcoming these disadvantages, OTE sound processors have conventionally had their own disadvantage of being incompatible with microphones configured to be held in place near an entrance to an ear canal of the recipient's ear.

U.S. Patent Application No. 2014/0233775A1 ("Hartley") discloses a modular adapter assembly used with a body-worn sound processor for telecoil and auxiliary audio input device mixing. Hartley discloses a BTE apparatus configured to be communicatively coupled to a telecoil and an auxiliary audio input device (e.g., a microphone worn near the ear), and a multi-position switch configured to selectively enable the telecoil and/or the auxiliary audio input device when the switch is in different positions. The contents of this application are hereby incorporated by reference in their entirety.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIG. 3 illustrates an exemplary implementation of the cochlear implant system of FIG. 1 that employs an off-the-ear ("OTE") sound processor according to principles described herein.

FIGS. 4A and 4B illustrate various aspects of the OTE sound processor of FIG. 3 according to principles described herein.

FIG. 5 illustrates another exemplary implementation of the cochlear implant system of FIG. 1 that employs an OTE sound processor along with a microphone assembly that positions a microphone near the entrance to the ear canal according to principles described herein.

FIGS. 6A through 6D illustrate various exemplary implementations of the microphone assembly of FIG. 5 according to principles described herein.

FIGS. 7A through 7D illustrate various additional exemplary implementations of the microphone assembly of FIG. 5 according to principles described herein.

DETAILED DESCRIPTION

Figure 1:
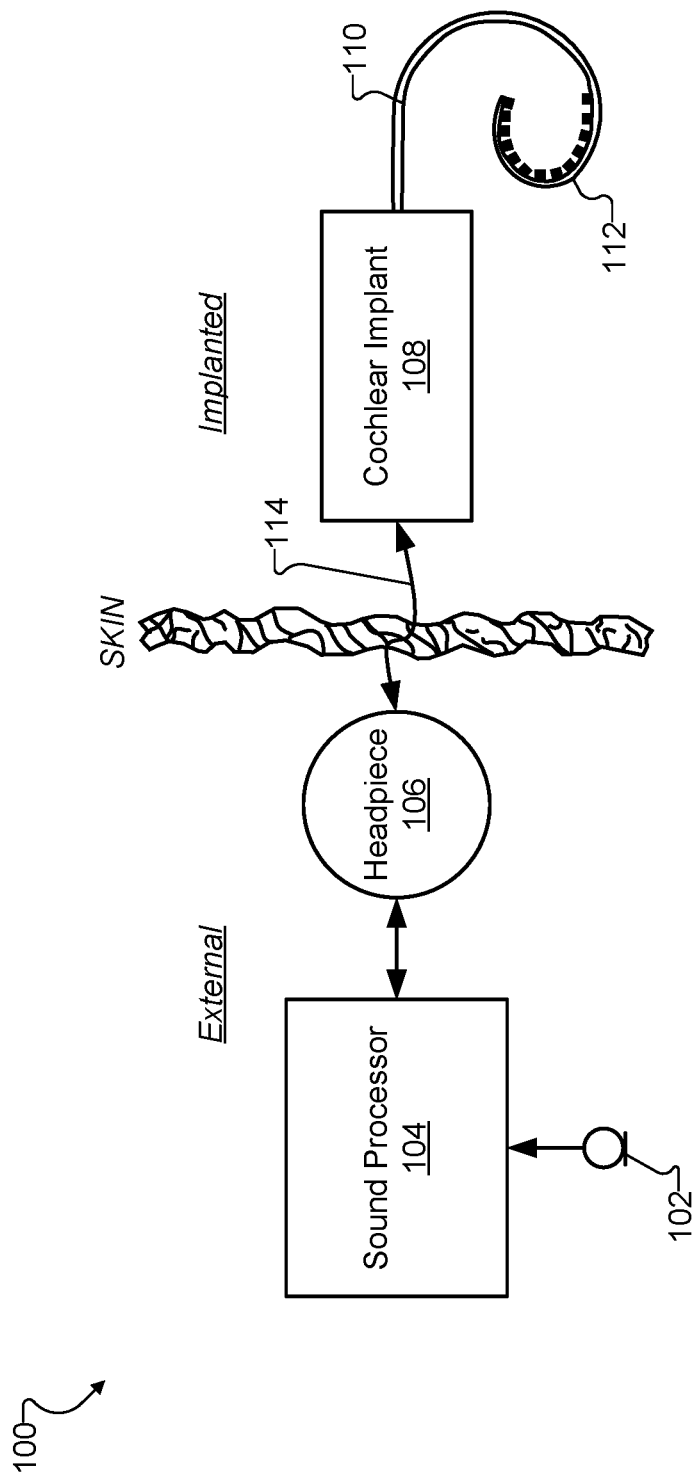
FIG. 1 illustrates an exemplary cochlear implant system according to principles described herein.

Cochlear implant systems and methods employing microphones near the ear with off-the-ear ("OTE") sound processors are described herein. For instance, in certain implementations, an exemplary cochlear implant system for use by a recipient may include a microphone assembly and an OTE sound processor communicatively coupled with the microphone assembly. The microphone assembly may include a microphone configured to capture an audio signal representative of sound presented to the recipient and a retention device configured to hold the microphone in place near an entrance to an ear canal of an ear of the recipient. For instance, the retention device may hold the microphone in place at (e.g., within, near, touching, etc.) a concha of the recipient's ear immediately external to the ear canal. In this way, the microphone may capture the sound presented to the recipient as the sound is naturally funneled toward the ear canal by the pinna of the ear. As such, the microphone may be positioned so as to capture approximately the same sound as naturally enters the ear canal, thereby utilizing natural sound funneling and filtering mechanisms that would be provided by the ear in an unassisted hearing scenario.

The OTE sound processor included in this exemplary cochlear implant system may include a housing configured to be worn on a head of the recipient at a location that is off the ear of the recipient. That is, rather than being hooked behind the ear as a behind-the-ear ("BTE") sound processor would be, and rather than being clipped to clothing or otherwise worn on the body of the recipient as a body-worn sound processor would be, the OTE sound processor may be worn on the head of the recipient away from the ear. For instance, in some examples, the OTE sound processor may be integrated with the headpiece (i.e., may include circuitry and components capable of implementing the headpiece functionality) and may be worn on the head at a conventional location of the headpiece (e.g., on the head at or near an implantation site of a cochlear implant). The OTE sound processor may further include electronic circuitry located within the housing. The electronic circuitry may be configured to generate stimulation parameters that, when transmitted to a cochlear implant implanted within the recipient, direct the cochlear implant to apply electrical stimulation representative of the captured audio signal to the recipient.

Cochlear implant systems and methods described herein that employ microphones near the ear with OTE sound processors may provide various benefits and advantages for cochlear implant system recipients. For example, cochlear implant systems and methods described herein may provide all the benefits and advantages of OTE sound processors together with all the benefits and advantages of microphones located at the entrance to the ear canal. While certain conventional cochlear implant systems and methods have provided the advantages of either OTE sound processors or microphones located at the entrance to the ear canal, conventional systems and methods have not provided all the advantages together in a single system. These sets of benefits and advantages will now be described.

OTE sound processors may be advantageous over other types of sound processors in several respects. For example, as mentioned above, relatively heavy and/or conspicuous BTE sound processors may be burdensome, unsightly, or otherwise undesirable for certain recipients. Similarly, body-worn sound processors may be associated with a different set of disadvantages. For example, while body-worn sound processors may help avoid a burdensome weight to be carried all day on the ear, and may be less conspicuous in certain respects (e.g., the sound processor itself may be hidden in a pocket or clipped inconspicuously to the clothing), body-worn sound processors may require inconvenient and unsightly cabling that extends from the body-worn sound processor to the headpiece and/or to other hardware worn on the head.

In contrast, head-worn OTE sound processors may avoid these disadvantages. For example, because they may be integrated with the headpiece and worn at an implantation site of the cochlear implant (off the ear and further back on the head), OTE sound processors may avoid placing any burden on the ear of the recipient and may instead attach to the head using the same method as the headpiece (e.g., attaching magnetically, being held in place by way of a headband, etc.). The all-in-one, integrated look of a combination OTE sound processor/headpiece may also be preferable to some recipients over the two-part look of a BTE sound processor connected by way of a cable to a headpiece. Moreover, such an integrated combination of the sound processor and the headpiece may generally be more discrete and easier to cover or hide (e.g., using hair, headwear, etc.) if the recipient should wish to do so.

Additionally, by combining a sound processor and a headpiece into an integrated OTE sound processor, the typical cable that runs between the sound processor and the headpiece may be eliminated, which may provide further convenience and/or aesthetic appeal for certain recipients as compared to cochlear implant systems including BTE or body-worn sound processors. Waterproofing procedures may also be made possible or more convenient when an integrated, all-in-one device is used to perform sound processing and headpiece functionality rather than a multi-component system. For example, a waterproof kit (e.g., a small bag or other container configured to fit the integrated OTE sound processor) may be provided to protect the OTE sound processor while exposed to water (e.g., while the recipient is showering, swimming, etc.).

Microphones located near the ear (i.e., microphones located at the entrance to the ear canal) may also be associated with various advantages. For example, as mentioned above, one advantage of such microphones or microphone placement is that the pinna of the ear performs natural funneling and filtering of sound that can only be fully taken advantage of by a microphone placed at the epicenter of this funneling and filtering (i.e., at the entrance to the ear canal). Moreover, microphones physically coupled to the ear may be less prone to shift and move around during operation than microphones attached to the head at other locations (e.g., integrated into OTE sound processors), which may be advantageous for remaining consistent and calibrated (e.g., for beamforming calibration or the like).

Additionally, other advantages of having a microphone located at the entrance to the ear canal relate to a pervasive assumption in the world that people hear with their ears, rather than with microphones located at other places on their bodies. For example, telephones, headsets, and other devices commonly used to provide sound for professional, educational, and/or entertainment purposes may be designed to direct sound into the ear canal, and may thus be configured to be positioned at or attached to the ear (rather than to a different spot on the head or elsewhere). Accordingly, conventional OTE sound processors that include microphones at other places on the head besides at the ear canal may thus be difficult to use with such devices because recipients may be required to hold the devices up to the microphone rather than up to their ears. It may be awkward, difficult, and/or embarrassing to hold a telephone earpiece to a microphone on one's head rather than to hold it up to the ear in accordance with its intended use and design.

Various embodiments will now be described in more detail with reference to the figures. The disclosed systems and methods may provide one or more of the benefits mentioned above and/or various additional and/or alternative benefits that will be made apparent herein.

FIG. 1 illustrates an exemplary cochlear implant system 100. As shown, cochlear implant system 100 may include a microphone 102, a sound processor 104, a headpiece 106, a cochlear implant 108, and an electrode lead 110 that includes a plurality of electrodes 112 disposed thereon. As shown, electrode lead 110 may be pre-curved so as to properly fit within the spiral shape of the cochlea. Additional or alternative components may be included within cochlear implant system 100 as may serve a particular implementation.

As shown, cochlear implant system 100 may include various components configured to be located external to a recipient including, but not limited to, microphone 102, sound processor 104, and headpiece 106. Cochlear implant system 100 may further include various components configured to be implanted within the recipient including, but not limited to, cochlear implant 108 and electrode lead 110.

Microphone 102 may be configured to detect audio signals presented to the recipient. Microphone 102 may be implemented in any suitable manner. For example, in certain implementations, microphone 102 may be implemented by a T-MIC™ microphone from Advanced Bionics, or another such microphone configured to be held in place at a location near the entrance to the ear canal (i.e., at or within the concha of the ear). In other implementations, microphone 102 may be implemented by one or more microphones disposed within headpiece 106, one or more microphones disposed within sound processor 104, one or more beamforming microphones, and/or any other suitable microphone or microphones as may serve a particular implementation. Additionally, in certain examples, microphone 102 may be implemented by a plurality of microphones including a microphone held in place at the entrance to the ear canal and one or more additional microphones disposed elsewhere within cochlear implant system 100. Examples of microphone configurations and placements for cochlear implant system 100 and various implementations thereof will be described in more detail below.

Sound processor 104 may be configured to direct cochlear implant 108 to generate and apply electrical stimulation (also referred to herein as "stimulation current") representative of one or more audio signals (e.g., signals generated by microphone 102, input by way of an auxiliary audio input port, input by way of a clinician's programming interface ("CPI") device, etc.) to one or more stimulation sites associated with an auditory pathway such as the auditory nerve of the recipient. Exemplary stimulation sites include, but are not limited to, one or more locations within the cochlea, the cochlear nucleus, the inferior colliculus, and/or any other nuclei in the auditory pathway. To this end, sound processor 104 may process the one or more audio signals in accordance with a selected sound processing strategy or program to generate appropriate stimulation parameters for controlling cochlear implant 108. Sound processor 104 may be housed within any suitable housing configured to be worn in various ways. For instance, in different types of implementations of cochlear implant system 100, sound processor 104 may be configured to be worn behind the ear of the recipient (a BTE sound processor), to be worn on the body (a body-worn sound processor), to be integrated with headpiece 106 and worn on the head at a location off the ear (an OTE sound processor), and/or to be worn in other locations or in other manners as may serve a particular implementation.

In some examples, sound processor 104 may wirelessly transmit stimulation parameters (e.g., in the form of data words included in a forward telemetry sequence) and/or power signals to cochlear implant 108 by way of a wireless communication link 114 between headpiece 106 and cochlear implant 108 (e.g., a wireless link between a coil disposed within headpiece 106 and a coil included within or physically coupled to cochlear implant 108). Communication link 114 may include a bi-directional communication link and/or one or more dedicated uni-directional communication links as may serve a particular implementation.

Headpiece 106 may be communicatively coupled to sound processor 104 and may include an antenna (e.g., a coil and/or one or more wireless communication components) configured to facilitate selective wireless coupling of sound processor 104 to cochlear implant 108. Headpiece 106 may additionally or alternatively be used to selectively and wirelessly couple any other external device to cochlear implant 108. To this end, headpiece 106 may be configured to be affixed to the recipient's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transmitted between sound processor 104 and cochlear implant 108 via communication link 114.

Cochlear implant 108 may include any type of implantable stimulator that may be used in association with the systems and methods described herein. For example, cochlear implant 108 may be implemented by an implantable cochlear stimulator. In some alternative implementations, cochlear implant 108 may include a brainstem implant and/or any other type of cochlear implant that may be implanted within a recipient and configured to apply stimulation to one or more stimulation sites located along an auditory pathway of a recipient.

In some examples, cochlear implant 108 may be configured to generate electrical stimulation representative of an audio signal processed by sound processor 104 (e.g., an audio signal captured by microphone 102) in accordance with one or more stimulation parameters transmitted thereto by sound processor 104. Cochlear implant 108 may be further configured to apply the electrical stimulation to one or more stimulation sites (e.g., one or more intracochlear regions) within the recipient via electrodes 112 disposed along electrode lead 110. For example, an array of stimulating electrodes 112 disposed on a distal portion of electrode lead 110 may be configured to be located within and to stimulate the cochlea when the distal portion of electrode lead 110 is inserted into the cochlea.

In some examples, cochlear implant 108 may include a plurality of independent current sources each associated with a channel defined by one or more of electrodes 112. In this manner, different stimulation current levels may be applied to multiple stimulation sites simultaneously by way of multiple electrodes 112.

Figure 2:
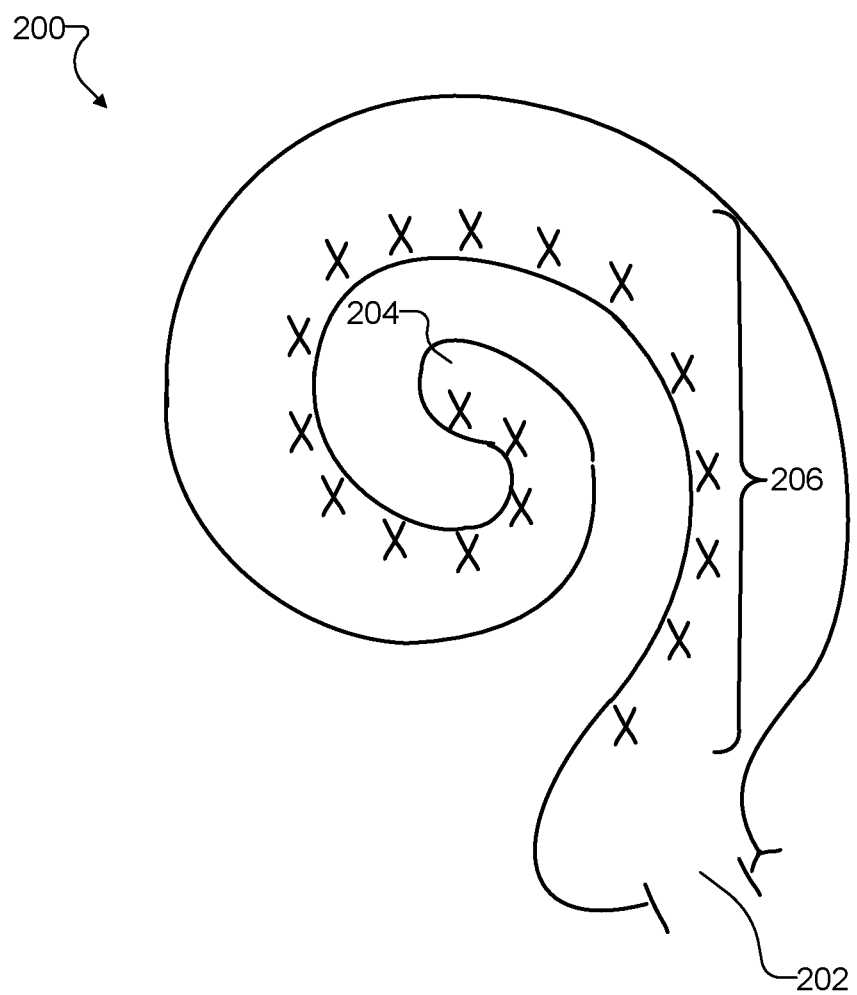
FIG. 2 illustrates a schematic structure of the human cochlea according to principles described herein.

FIG. 2 illustrates a schematic structure of the human cochlea 200 into which electrode lead 110 may be inserted. As shown in FIG. 2, cochlea 200 is in the shape of a spiral beginning at a base 202 and ending at an apex 204. Within cochlea 200 resides auditory nerve tissue 206, which is denoted by Xs in FIG. 2. The auditory nerve tissue 206 is organized within the cochlea 200 in a tonotopic manner. Relatively low frequencies are encoded at or near the apex 204 of the cochlea 200 (referred to as an "apical region") while relatively high frequencies are encoded at or near the base 202 (referred to as a "basal region"). Hence, electrical stimulation applied by way of electrodes disposed within the apical region (i.e., "apical electrodes") may result in the recipient perceiving relatively low frequencies and electrical stimulation applied by way of electrodes disposed within the basal region (i.e., "basal electrodes") may result in the recipient perceiving relatively high frequencies. The delineation between the apical and basal electrodes on a particular electrode lead may vary depending on the insertion depth of the electrode lead, the anatomy of the recipient's cochlea, and/or any other factor as may serve a particular implementation.

FIG. 3 illustrates an exemplary implementation of cochlear implant system 100 that employs an OTE sound processor. This implementation of cochlear implant system 100 will be referred to herein as cochlear implant system 300.

Within cochlear implant system 300, microphone 102 described above is implemented by one or more built-in microphones 302, while both sound processor 104 and headpiece 106 described above are implemented by an OTE sound processor 304. Implanted components of cochlear implant system 100 described above such as cochlear implant 108 and electrode lead 110 will be understood to be included in cochlear implant system 300 so as to perform the same functionality as described above.

In some examples, OTE sound processor 304 may be implemented as an all-in-one active headpiece configured to perform the functionality of both sound processor 104 and headpiece 106 described above. For example, OTE sound processor 304 may be included within a housing configured to be worn at a location off the ear of the recipient (e.g., at an implantation site of cochlear implant 108), and may include, within the housing, not only electronic circuitry for performing the functionality of sound processor 104, but also circuitry for performing the functionality of headpiece 106. For example, OTE sound processor 304 may include, within the housing, an antenna configured to transcutaneously transmit stimulation parameters from the electronic circuitry implementing sound processor 104 to cochlear implant 108.

To illustrate, FIGS. 4A and 4B show various aspects of OTE sound processor 304. As will be described, the exemplary implementation of OTE sound processor 304 illustrated in FIGS. 4A and 4B, as well as other implementations in other figures herein, may be integrated with (i.e., may include) integrated headpiece functionality. However, it will be understood that other exemplary implementations of OTE sound processor 304 may not include integrated headpiece functionality, but may still be worn on the head at a location off the ear. In such examples, OTE sound processor 304 may be closely associated with an external headpiece. For example, OTE sound processor 304 may be implemented within a housing that physically couples with a housing of an external headpiece, or may be physically and/or electrically coupled with the external headpiece. In the same or other examples, OTE sound processor 304 may employ the same or a similar mechanism for attaching to the head of the recipient. For example, OTE sound processor 304 and the external headpiece could both attach using separate or shared magnets, headbands, or the like.

As depicted by the implementation in FIG. 4A, OTE sound processor 304 may include a housing 402 constructed of a suitable material for enclosing components such as electronic circuitry 404, an audio interface 406, an antenna coil 408, a magnet 410, and/or one or more built-in microphones 302. Each of the components included within OTE sound processor 304 will now be described.

Electronic circuitry 404 may include one or more computing components (e.g., a processor, a memory within which instructions to be performed by the processor may be stored, etc.) and/or other electronic components configured to perform or direct any of the operations described in relation to sound processor 104, headpiece 106, or cochlear implant 108. For example, electronic circuitry 404 may be configured to receive an audio signal (i.e., an analog or digital signal captured by built-in microphones 302, received by way of audio interface 406, etc.), divide the audio signal into a plurality of channels each associated with audio components within different frequency bands, and generate stimulation parameters corresponding with each of the channels. Electronic circuitry 404 may then send the stimulation parameters, along with electrical power configured to power cochlear implant 108, through the recipient's skin to be received by cochlear implant 108. In certain examples, electronic circuitry 404 may further perform other operations as may serve a particular implementation. For instance, in certain implementations, electronic circuitry 404 may perform front-end processing operations that will be described in more detail below.

Audio interface 406 may be configured to receive an audio signal (e.g., a microphone signal, a line-in signal, etc.) from a source external to OTE sound processor 304. To this end, audio interface 406 may include any electrical or mechanical components as may serve a particular implementation, and may function in any suitable way. For example, audio interface 406 may include or be associated with a cable physically connected to an external audio source (e.g., a microphone assembly or other suitable source as will be described in more detail below), or may implement a wireless interface (e.g., a Bluetooth interface or the like) configured to receive audio signals wirelessly. In some examples, audio interface 406 may include a connector allowing a cable to be removably coupled to OTE sound processor 304. Any audio signal received by way of audio interface 406 may be provided to electronic circuitry 404 for processing in the ways described above.

Antenna coil 408 may be configured to help perform the functionality described above in relation to headpiece 106. Specifically, for example, antenna coil 408 may, under direction from electronic circuitry 404, be configured to transcutaneously transmit stimulation parameters from electronic circuitry 404 to cochlear implant 108. Such outgoing transmission to cochlear implant 108 may be referred to as forward telemetry. Additionally, in some examples, antenna coil 408 (or a second antenna coil not explicitly shown) may further facilitate backward telemetry in which OTE sound processor 304 receives a transcutaneous transmission sent by cochlear implant 108 in a similar way. In these examples, the signal may be provided to and used by electronic circuitry 404 to perform sound processing operations.

Magnet 410 may be used to physically couple OTE sound processor 304 to the head at an implantation site of cochlear implant 108, and to hold OTE sound processor 304 in place at that location. For example, by way of magnet 410, housing 402 may be configured to be worn on the head of the recipient at a location that is off the ear (i.e., that is not directly behind the ear and that does not touch the ear or rely on the ear to be held in place). It will be understood that, while magnet 410 provides one optional way for OTE sound processor 304 to be held in place on the head, other implementations of sound processor 304 may employ other methods of being held in place such as headbands, magnets built into the cochlear implant, or the like. As such, magnet 410 may be an optional component and housing 402 may be configured to be worn on the head at the location off the ear in any manner as may serve a particular implementation.

Built-in microphones 302 may include one or more microphones configured to capture sound presented to the recipient. In particular, microphones 302 may capture sound as the sound waves propagate to the off-the-ear location at which OTE sound processor 304 is worn. In some examples, audio signals captured by multiple microphones included within microphones 302 may be combined in accordance with a beamforming technique to create a directional audio signal. This may be useful, for example, in facilitating the recipient to understand speech originating from a source in one direction (e.g., directly in front of the recipient) while noise is originating from other directions (e.g., from other speakers in a crowded room in which the recipient is located).

In certain implementations, openings in housing 402 may allow sound to be captured more directly by microphones 302. For example, as shown in FIG. 4B, which depicts the exemplary external appearance of OTE sound processor 304, one microphone 302 labeled microphone 302-1 may be included behind a first opening in housing 402 while another microphone 302 labeled microphone 302-2 may be included behind a second opening in housing 402. As further illustrated in FIG. 4B, various buttons, light-emitting diodes ("LEDs"), and/or other use interface mechanisms for receiving input or providing output to a user (e.g., the recipient) may further be included on the external case of OTE sound processor 304.

OTE sound processor 304 may provide a recipient any of the benefits described above in relation to off-the-ear sound processors and all-in-one sound processor/headpiece devices. For example, OTE sound processor 304 may be less burdensome and/or conspicuous to wear as compared to a BTE sound processor, may not require any cables, may be convenient and easy to waterproof before showering or swimming, and so forth. However, because microphones 302 are integrated with or built into OTE sound processor 304, OTE sound processor 304, on its own, may not be able to provide the benefits described above in relation to microphones placed near the entrance to the ear canal (e.g., T-MIC™ microphones from Advanced Bionics).

To remedy this, FIG. 5 illustrates another exemplary implementation of cochlear implant system 100 that employs OTE sound processor 304 and built-in microphones 302 along with a microphone assembly that positions a microphone near the entrance to the ear canal. This implementation of cochlear implant system 100 will be referred to herein as cochlear implant system 500.

As shown, along with the same implanted components (e.g., cochlear implant 108, electrode lead 110, etc.) and the same built-in microphones 302 and OTE sound processor 304 that have been discussed, cochlear implant system 500 further includes a microphone assembly 502 communicatively coupled with OTE sound processor 304 by way of a communication interface 504. Accordingly, cochlear implant system 500 depicts one example of a cochlear implant system that employs a microphone near the ear with an OTE sound processor. Specifically, microphone assembly 502 may include a microphone configured to capture an audio signal representative of sound presented to a recipient using cochlear implant system 500, and may further include a retention device configured to hold the microphone in place near an entrance to an ear canal of an ear of the recipient. Additionally, as described above, OTE sound processor 304 may be communicatively coupled with microphone assembly 502 by way of communication interface 504, and may include a housing configured to be worn on a head of the recipient at a location that is off the ear of the recipient. OTE sound processor 304 may also include, within the housing, electronic circuitry that is configured to generate stimulation parameters that, when transmitted to cochlear implant 108, direct cochlear implant 108 to apply electrical stimulation representative of the captured audio signal to the recipient.

While cochlear implant system 500, as depicted in FIG. 5, illustrates a cochlear implant system with at least two microphones (i.e., at least one microphone included within microphone assembly 502 and one or more microphones comprising built-in microphones 302), it will be understood that, in certain examples, the microphone or microphones included within microphone assembly 502 may replace built-in microphones 302 such that built-in microphones 302 may be omitted from the cochlear implant system. Such examples will be described in more detail below.

As described above, microphone assembly 502 may include a microphone configured to be held in place at a location near the entrance to the ear canal and a retention device (e.g., an ear hook, an earmold, etc.) for holding the microphone in place at the entrance to the ear canal. Additionally, as will be described in more detail below, microphone assembly 502 may further include other components such as additional microphones, a power supply, a communication interface, circuitry for performing front-end processing operations, and the like. However, it will be understood that, regardless of which of these components may be included within microphone assembly 502, microphone assembly 502 may be distinguished from several particular devices that may be used in certain conventional cochlear implant systems.

For example, microphone assembly 502 is not implemented by a microphone extension accessory configured to plug into a BTE sound processor (e.g., a T-MIC™ accessory built for a BTE sound processor) because, in that case, the BTE sound processor, rather than microphone assembly 502, would implement the retention device (i.e., because the BTE sound processor would be configured to attach to the ear and thereby hold the microphone extension accessory in place). Moreover, while microphone assembly 502 may be worn at the ear using an ear hook and may include front-end processing circuitry, microphone assembly 502 is not implemented by a full BTE sound processor that includes electronic circuitry for behind-the-ear generation and application of stimulation parameters. To the contrary, the purpose of microphone assembly 502 is to provide an audio signal (e.g., a raw microphone signal or a preprocessed audio signal that has gone through front-end processing as will be described in more detail below) to OTE sound processor 304, which is worn on the head at the off-the-ear location, to perform the generation and application of the stimulation parameters. As yet another example, microphone assembly 502 is not implemented by a behind-the-ear accessory configured to communicatively couple a body-worn sound processor to a headpiece and/or to perform switching operations for such a system, such as the modular adapter assembly mentioned above. To the contrary, as mentioned above, microphone assembly 502 is configured to capture and provide an audio signal directly to an OTE sound processor that is worn on the head at a location off the ear of the recipient (e.g., to OTE sound processor 304).

As mentioned above, cochlear implant system 500 may be configured to perform certain front-end processing operations on audio signals captured by any microphones in the system. For example, front-end processing operations may involve combining audio signals captured from multiple microphones (e.g., to mix the signals, to perform beamforming techniques on the signals to generate a directional audio signal, etc.), performing equalization operations on the signals (e.g., to emphasize or deemphasize certain frequencies according to a preference of a recipient), or the like. As mentioned above, while front-end processing involves "processing" sound in a sense of the word, front-end processing operations may be clearly distinguished from operations that are performed only by a "sound processor" such as OTE sound processor 304. Specifically, front-end processing operations do not include, for instance, dividing audio signals into various channels to generate stimulation parameters for each channel, or transmitting the stimulation parameters to cochlear implant 108 to direct cochlear implant 108 to apply electrical stimulation based on the stimulation parameters.

While these types of sound processing operations are specifically performed by a sound processor (e.g., OTE sound processor 304), front-end processing operations may be performed either by a microphone assembly or a sound processor, and may be used in connection with certain microphone input and/or certain modes of operation. For instance, in one example, the retention device of microphone assembly 502 may be implemented by an ear hook and may further include a plurality of additional microphones integrated into the ear hook. Additionally, front-end processing circuitry may also be integrated into the ear hook and configured to generate a combined audio signal based on a combination of additional audio signals captured by the plurality of additional microphones to represent the sound presented to the recipient. In this example, electronic circuitry 404 included within OTE sound processor 304 may be configured to generate the stimulation parameters when operating in a first mode, and may be further configured, when operating in a second mode, to generate additional stimulation parameters that, when transmitted to cochlear implant 108, direct cochlear implant 108 to apply electrical stimulation representative of the combined audio signal.

As another example, in implementations where OTE sound processor 304 includes a plurality of additional microphones within the housing (e.g., a plurality of built-in microphones 302), front-end processing circuitry also included within the housing may be configured to generate a combined audio signal based on a combination of additional audio signals captured by the plurality of built-in microphones 302 to represent the sound presented to the recipient. Here again, electronic circuitry 404 within OTE sound processor 304 may be configured to generate stimulation parameters associated with the microphone of microphone assembly 502 when operating in a first mode, and may be further configured, when operating in a second mode, to generate additional stimulation parameters that, when transmitted to the cochlear implant, direct the cochlear implant to apply electrical stimulation representative of the combined audio signal (i.e., from built-in microphones 302).

To further illustrate microphone assembly 502, FIGS. 6A-6D and 7A-7D illustrate various exemplary implementations of microphone assembly 502 that may be employed in various implementations of cochlear implant system 500. In particular, FIGS. 6A-6D illustrate implementations of microphone assembly 502 that employ an ear hook as a retention device, while FIGS. 7A-7D illustrate implementations of microphone assembly 502 that employ an earmold as the retention device. It will be understood that the implementations of microphone assembly 502 illustrated in FIGS. 6A-6D and 7A-7D are exemplary only, and that other implementations of microphone assembly 502 may be employed as may serve a particular implementation of cochlear implant system 500. For example, other implementations of microphone assembly 502 may employ additional features (e.g., additional microphones, a waterproof or water-resistant housing, etc.), additional combinations of features, different types of retention devices, or the like.

A simple numbering scheme is used in FIGS. 6A-6D and 7A-7D to differentiate like components in certain implementations from others. Specifically, the implementations of microphone assembly 502 in FIGS. 6A-6D are respectively designated by reference numbers ending in "-1" through "-4," while the implementations of microphone assembly 502 in FIGS. 7A-7D are respectively designated by reference numbers ending in "-5" through "-8." For example, as shown, FIG. 6A depicts an implementation of microphone assembly 502 referred to as microphone assembly 502-1 and that includes various components ending with "-1," FIG. 6B depicts an implementation of microphone assembly 502 referred to as microphone assembly 502-2 and that includes various components ending with "-2," and so forth until FIG. 7D, which depicts an implementation of microphone assembly 502 referred to as microphone assembly 502-8 and that includes various components ending with "-8."

In the implementations of microphone assembly 502 illustrated in FIGS. 6A-6D and 7A-7D (i.e., microphone assemblies 502-1 through 502-8), various components may be included, as will now be described.

First, as shown, each implementation of microphone assembly 502 may include a microphone 602 (i.e., microphones 602-1 through 602-8). Each respective microphone 602 may be configured to capture an audio signal representative of sound presented to the recipient by, for example, generating the audio signal (e.g., as an electrical signal) based on sound detected by the microphone 602 at the location near the entrance to the ear canal of the ear of the recipient, where the microphone 602 is located.

Respective retention devices may be configured to hold the respective microphones 602 in place near the entrance to the ear canal. For example, in FIGS. 6A-6D, the retention devices configured to hold respective microphones 602 in place near the entrance to the ear canal of the ear are implemented by an ear hook, and thus include respective booms 604 (i.e., booms 604-1 through 604-4) connected to respective ear hooks 606 (i.e., ear hooks 606-1 through 606-4). These retention devices are configured to be supported by the ear itself, such as by hanging from the pinna of the ear. In some examples, booms 604 and ear hooks 606 may take different forms than those shown in FIGS. 6A-6D. For example, the retention device may include an ear hook that forms a full loop that encircles the entire ear, or the like.

In contrast, the examples illustrated in FIGS. 7A-7D show retention devices configured to hold the respective microphones 602 in place near the entrance to the ear canal of the ear that are implemented by respective earmolds 702 (i.e., earmolds 702-5 through 702-8). Earmolds 702 may be implemented as custom earmolds configured to fit snugly within the ear of a particular recipient, or, in other implementations, may be implemented as general use earmolds configured to fit in ears of a variety of different recipients (e.g., such as by using silicone earbuds, earbud tips, etc.).

Each implementation of microphone assembly 502 may include a communication interface 608 (i.e., communication interfaces 608-1 through 608-8) for communicating audio signals captured by respective microphones 602. However, as shown, different microphone assemblies 502 may have different types of communication interfaces 608 (e.g., wired communication interfaces 608-1, 608-3, 608-5, and 608-7 or wireless communication interfaces 608-2, 608-4, 608-6, and 608-8).

Microphone assemblies 502 that have wireless communication interfaces 608 (e.g., microphone assemblies 502-2, 502-4, 502-6, and 502-8) may require respective power supplies 610 (i.e., power supplies 610-2, 610-4, 610-6, and 610-8, respectively) for powering respective wireless transmitters 612 (i.e., wireless transmitters 612-2, 612-4, 612-6, and 612-8, respectively) that implement the wireless communication interfaces 608. Specifically, wireless transmitters 612 may be configured to wirelessly transmit, based on power supplied by respective power supplies 610, the audio signal captured by respective microphones 602 to electronic circuitry 404 of OTE sound processor 304 in cochlear implant system 500. Wireless transmitters 612 may be implemented using Bluetooth technology or any other suitable wireless technology as may serve a particular implementation.

In contrast, microphone assemblies 502 that have wired communication interfaces 608 (e.g., microphone assemblies 502-1, 502-3, 502-5, and 502-7) may not require a wireless transmitter 612 or a power supply 610 for powering it (as described below, a power supply 610 may still be included in some examples for powering other components). For example, cochlear implant system 500 may include a cable configured to electrically connect the respective microphone 602 of the microphone assembly 502 to electronic circuitry 404 of OTE sound processor 304, and OTE sound processor 304 may be communicatively coupled with the microphone assembly 502 by way of a wired interface 608 implemented by the cable. Certain recipients may prefer a wireless interface for the reasons described above (e.g., since cables running from a BTE device to an OTE device may be inconvenient or unsightly, etc.). However, for certain recipients and/or in certain contexts, wired interfaces may also provide certain advantages. For instance, wired interfaces may be less expensive and more reliable than wireless interfaces in certain examples, and may not require a power supply 610, thereby potentially leading to a smaller, more convenient, and/or lighter weight microphone assembly 510 (e.g., as illustrated by the relatively small size of microphone assembly 502-1 in comparison to other microphone assemblies 502 that employ respective power supplies).

A respective power supply 610 may also be employed in implementations of microphone assembly 502 that include front-end processing circuitry 614 (e.g., front-end processing circuitry 614-3, 614-4, 614-7, or 614-8). For example, power supplies 610-3 and 610-7 are included, respectively, within microphone assemblies 502-3 and 502-7 to provide power for front-end processing circuitry 614-3 and 614-7. In some examples, such as illustrated by microphone assemblies 502-4 and 502-8, respective power supplies 610 may be employed to provide power for both a wireless transmitter 612 and front-end processing circuitry 614.

Where front-end processing circuitry 614 is included within an implementation of microphone assembly 502, the circuitry may be employed to perform any of the front-end processing operations described herein. For example, as described above, front-end processing circuitry 614 may be configured to equalize or otherwise alter and preprocess audio signals (e.g., raw microphone signals), to mix or otherwise combine individual audio signals to form combined audio signals, to perform beamforming operations, or the like.

Figure 8:
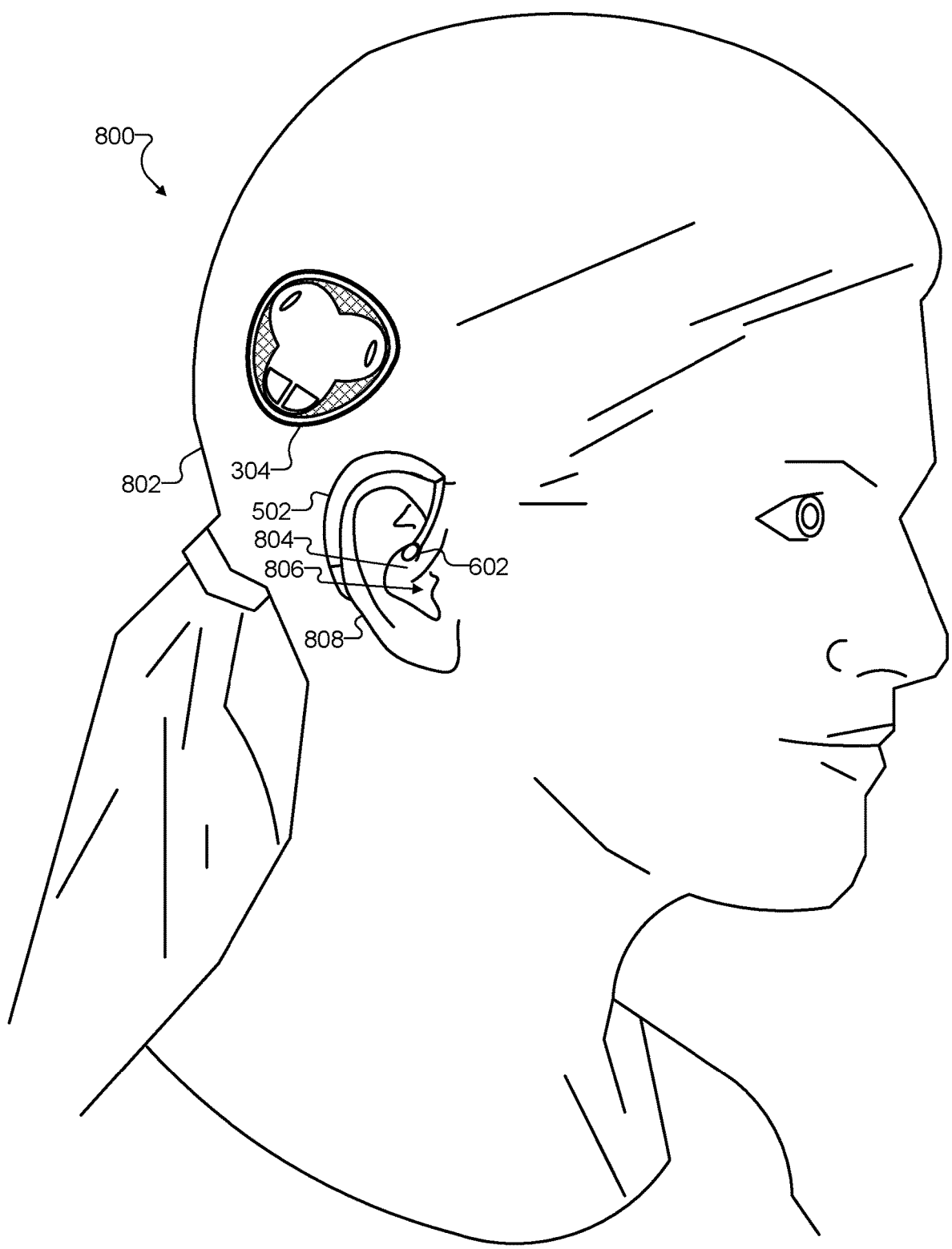
FIG. 8 illustrates an exemplary operational configuration of the cochlear implant system of FIG. 5 while being worn by a recipient according to principles described herein.

FIG. 8 illustrates an exemplary operational configuration 800 of cochlear implant system 500 while being worn by a recipient 802. Specifically, as shown, OTE sound processor 304 is shown to be worn on the head of recipient 802 at a location off the ear. For example, the position at which OTE sound processor 304 is located may be at a location of an implantation site of cochlear implant 108 (not explicitly shown in FIG. 8 but understood to be implanted beneath the skin of the head at the implantation site).

As further illustrated, microphone assembly 502 may be placed at the ear of recipient 802. In the example of operational configuration 800, for instance, microphone assembly 502 may be implemented using an ear hook design so as to hang on the ear of recipient 802 while holding microphone 602 in place at a concha 804 of the ear, near an ear canal 806. As used herein, a microphone may be referred to as being located "near an entrance to the ear canal" of a recipient's ear when, as illustrated with microphone 602 in FIG. 8, the microphone is positioned to reside at the concha of the recipient's ear. In some examples, the microphone may touch the tissue of the concha. In other examples, the microphone may hover just over the tissue within the space defined by the concha. In any case, as depicted by the proximity of microphone 602 to the entrance of ear canal 806, the location of microphone 602 at concha 804 may be near enough to ear canal 806 that a pinna 808 of the ear naturally funnels sound toward the location of microphone 602 such that the microphone detects a similar or identical version of sound as propagates into ear canal 806. Moreover, the location of microphone 602 may be between the ear of recipient 802 and an earpiece of a communications handset (e.g., a telephone or the like) when the earpiece is positioned at the ear.

While only a right side of the head of recipient 802 is illustrated in FIG. 8, it will be understood that a second cochlear implant system 500 similar to the implementation illustrated in FIG. 8 may be employed by recipient 802 at her left ear. Specifically, for example, if recipient 802 suffers from hearing loss in both ears, a second cochlear implant may be implanted on the other side of her head that may be associated with a second sound processor (e.g., a second OTE sound processor), a second microphone (e.g., a second microphone assembly configured to be worn at the left ear), and so forth.

Alternatively, if recipient 802 has a cochlear implant only on the right side of her head (e.g., at the implantation site under OTE sound processor 304), cochlear implant system 500 may include only the one OTE sound processor 304, but may further include a contralateral microphone assembly similar to microphone assembly 502. For example, the contralateral microphone assembly may include a contralateral microphone configured to capture a contralateral audio signal representative of the sound presented to the recipient and a contralateral retention device configured to hold the contralateral microphone in place near an entrance to an ear canal of an opposite ear of recipient 802 (i.e., an ear canal of the left ear).

In this example, OTE sound processor 304 may be further communicatively coupled with the contralateral microphone assembly so as to further receive the contralateral audio signal along with the audio signal provided by microphone assembly 502. For example, electronic circuitry 404 within OTE sound processor 304 may be configured to generate the stimulation parameters so as to direct the cochlear implant to apply electrical stimulation that not only represents the captured audio signal at the right side, but is further representative of the contralateral audio signal captured at the left side of the recipient. In this way, recipients who suffer from bilateral hearing loss but have only a unilateral cochlear implant system may enjoy increased sound quality for sounds originating from any direction (i.e., due to decreased head shadow effects), may hold a communications handset up to either ear or switch between ears, and/or enjoy other such benefits.

Recipient 802 may enjoy various benefits described herein by wearing OTE sound processor 304 on her head as shown, rather than employing, for example, a BTE sound processor or body-worn sound processor. Moreover, cochlear implant system 500 allows recipient 802 to enjoy many of those advantages while also adding various benefits, also described herein, of having a microphone placed at the ear canal using microphone assembly 502. For example, recipient 802 may use microphone assembly 502 while using a telephone and/or at times when she prioritizes authentic sound capture over other considerations.

However, in certain contexts, recipient 802 may still desire to maximize the benefits of wearing OTE sound processor 304 on the head by not wearing anything (e.g., even including microphone assembly 502) behind the ear. For example, if microphone assembly 502 includes a wired communication interface implemented by a cable (not shown in the example of FIG. 8), recipient 802 may wish to eliminate the cable when engaging in activities such as sports where the cable could be snagged and the benefits offered by the placement of microphone 602 at concha 804 are less important. As another example, if recipient 802 plans to engage in an activity where cochlear implant system 500 will get wet (e.g., showering, swimming, etc.), it may be desirable to consolidate all of the external components of cochlear implant system 500 into a single device that can be conveniently protected (e.g., by inserting it into a waterproof case or the like). As yet another example, recipient 802 may enjoy having microphone 602 located near the entrance to ear canal 806 during the work day when she often uses a telephone handset to do her job, but may prefer to not have anything on her ear after the work day is done.

To this end, it may be desirable for microphone assembly 502 to be modular and/or flexible to accommodate different wearing scenarios for different situations. In particular, it may be desirable for microphone assembly 502 to be wearable behind the ear as shown in FIG. 8 in certain situations, while being integrated with (physically connected to) OTE sound processor 304 in other situations. For instance, in one implementation, it may be desirable for electronic circuitry 404 within OTE sound processor 304 to be configured to operate in either a first mode (e.g., a mode associated with a microphone located near the entrance to the ear canal) or a second mode (e.g., a mode associated with microphones not located near the entrance to the ear canal). In such an implementation, microphone assembly 502 may be configured to be worn on the ear of recipient 802 such that the retention device holds microphone 602 in place near the entrance to ear canal 806 of the ear when electronic circuitry 404 operates in the first mode, and microphone assembly 502 may be further configured to be worn off the ear of the recipient (e.g., by physically attaching to housing 402 of OTE sound processor 304) when electronic circuitry 404 operates in the second mode.

Figure 9A:
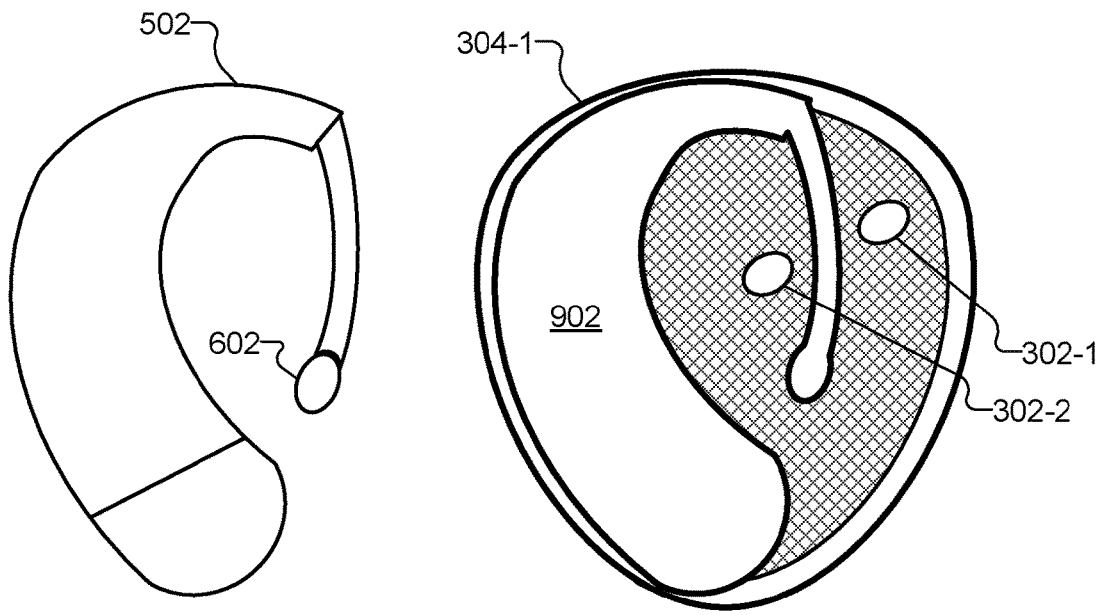
FIGS. 9A and 9B illustrate additional exemplary implementations of the microphone assembly and OTE sound processor of FIG. 5 according to principles described herein.
Figure 9B:
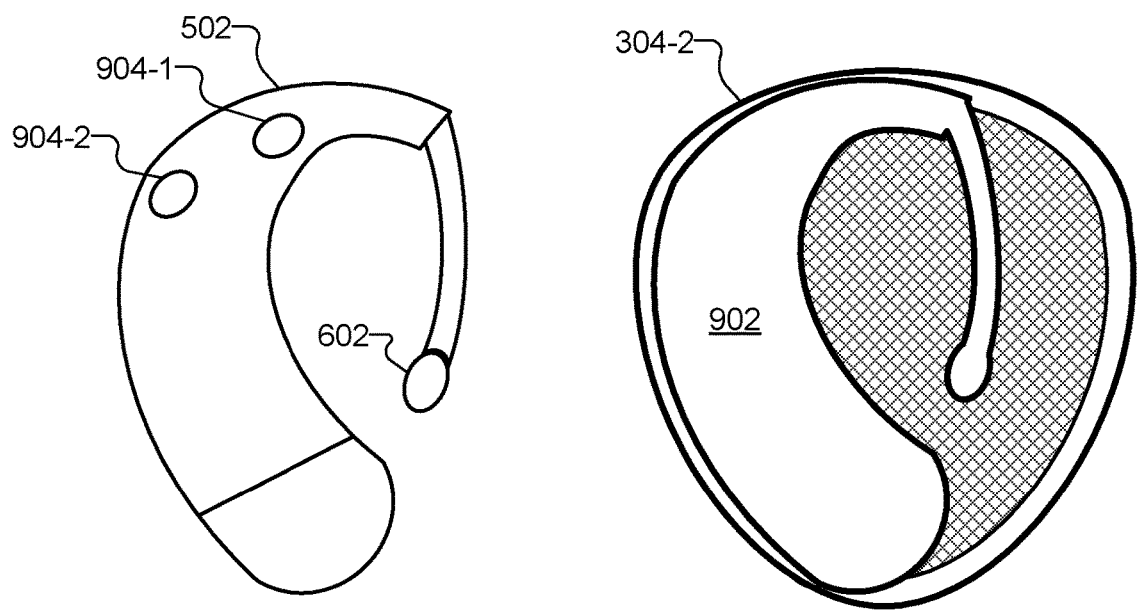

To illustrate, FIGS. 9A and 9B illustrate additional exemplary implementations of microphone assembly 502 and OTE sound processor 304 that are configured to be modular so as to allow recipient 802 to choose whether to wear microphone assembly 502 at the ear or to attach it to OTE sound processor 304 to thereby wear microphone assembly 502 on the head at a location off the ear when desired.

Specifically, as shown in FIG. 9A, an implementation of OTE sound processor 304 labeled OTE sound processor 304-1 may include the one or more built-in microphones 302 within the housing (e.g., having openings through the housing as shown), and the microphones 302 may be configured to capture additional audio signals representative of the sound presented to the recipient (e.g., as the sound propagates to the location of OTE sound processor 304). Electronic circuitry 404 may be configured to generate the stimulation parameters that direct cochlear implant 108 to apply the electrical stimulation representative of the audio signal captured by microphone 602 (i.e., the audio signal captured near the entrance to the ear canal) when operating in the first mode. Then, when operating in the second mode, electronic circuitry 404 may further be configured to generate stimulation parameters that, when transmitted to cochlear implant 108, direct cochlear implant 108 to apply electrical stimulation representative of the additional audio signals captured by microphones 302.

When operating in the second mode, microphone assembly 502 may be physically attached to OTE sound processor 304-1. For example, as shown, OTE sound processor 304-1 may include a retention cavity 902 configured to accommodate and hold microphone assembly 502, such as by allowing microphone assembly 502 to "snap into" or otherwise be placed within retention cavity 902. In some examples, rather than retention cavity 902, implementations of microphone assembly 502 and/or OTE sound processor 304 may employ other methods of allowing for physical attachment. For instance, a latching mechanism, an adhesive, a friction-based fastener, a hook and loop fastener, or any other suitable attachment mechanism may be used to physically couple and retain microphone assembly 502 with OTE sound processor 304-1. It will be understood that in examples in which a cable is used to provide a wired communication interface between microphone assembly 500 and OTE sound processor 304, the cable may be configured to disconnect from microphone assembly 502 and OTE sound processor 304 when in the second mode (i.e., when microphone assembly 502 is physically attached to OTE sound processor 304), or a cable well or the like may be included to accommodate the cable (not explicitly shown).

In the example of FIG. 9A, microphone assembly 502 is shown to be a purely optional accessory. For example, if microphone assembly 502 is not employed (e.g., is removed from the ear by recipient 802) in the example of FIG. 9A, OTE sound processor 304-1 may still have everything required to perform normal operations, the only difference being that microphones 302 will be used rather than microphone 602. Even if microphone assembly 502 is not required for operation in this example, however, it may still be convenient for microphone assembly 502 to be placed and held within retention cavity 902. In this way, recipient 802 may avoid losing microphone assembly 502 and may have it conveniently available whenever desired (e.g., if answering the phone or the like). Additionally, in some implementations, OTE sound processor 304-1 may be configured to use microphone 602 instead of or in addition to (e.g., in connection with) microphones 302 even when microphone assembly 502 is physically attached to OTE sound processor 304 (e.g., to optimize a directional audio signal by performing beamforming with all three microphones, etc.).

In other examples, microphone assembly 502 may not be an optional accessory, but, to the contrary, may be a required component necessary for normal system operation. This may be the case if microphone assembly 502 includes the only microphone or microphones in the cochlear implant system, the only front-end processing in the system, or the like. For example, in certain implementations, OTE sound processor 304 may not include any microphone 302, as mentioned above. In such implementations, microphone assembly 502 may include microphone 602, as well as one or more additional microphones configured to capture additional audio signals representative of the sound presented to the recipient. As with the example of FIG. 9A employing built-in microphones 302, electronic circuitry 404 may be configured to generate the stimulation parameters that direct cochlear implant 108 to apply the electrical stimulation representative of the audio signal captured by microphone 106 when operating in the first mode, while, when operating in the second mode, generating stimulation parameters that direct the cochlear implant to apply electrical stimulation representative of the additional audio signals captured by the additional microphones included within microphone assembly 502.

To illustrate, FIG. 9B shows an implementation of microphone assembly 502 that includes microphone 602 (configured to capture a first audio signal representative of sound presented to the recipient), an ear hook (configured to hold microphone 602 in place near an entrance to ear canal 806), a microphone 904-1 and a microphone 904-2 integrated into the ear hook (configured to capture, respectively, a second audio signal and a third audio signal representative of the sound presented to the recipient), and front-end processing circuitry integrated into the ear hook (configured to generate a combined audio signal based on a combination of the second and third audio signals). An implementation of OTE sound processor 304 labeled OTE sound processor 304-2 in FIG. 9B may be configured to communicatively couple with the implementation of microphone assembly 502. Like other implementations of OTE sound processor 304, OTE sound processor 304-2 may include a housing configured to be worn on a head of the recipient at a location that is off the ear of the recipient, and electronic circuitry included within the housing. In the case of OTE sound processor 304-2, the electronic circuitry may be configured to operate in either a first mode (in which the electronic circuitry generates stimulation parameters that, when transmitted to cochlear implant 108, direct cochlear implant 108 to apply electrical stimulation representative of the first audio signal to the recipient) or a second mode (in which the electronic circuitry generates stimulation parameters that, when transmitted to cochlear implant 108, direct cochlear implant 108 to apply electrical stimulation representative of the combined audio signal to the recipient).

In the example of FIG. 9B, microphone assembly 502 is configured to be worn on the ear of the recipient such that the retention device holds microphone 602 in place near the entrance to ear canal 806 when the electronic circuitry operates in the first mode. Microphone assembly 502 is further configured to be worn off the ear of the recipient (e.g., by physically attaching to the housing of OTE sound processor 304-2, such as by being snapped into retention cavity 902) when the electronic circuitry operates in the second mode. In either mode, however, microphones included within microphone assembly 502 (i.e., microphone 602 and/or microphones 904-1 and 904-2) may be used since OTE sound processor 304-2 does not include any built-in microphones.

Figure 10:
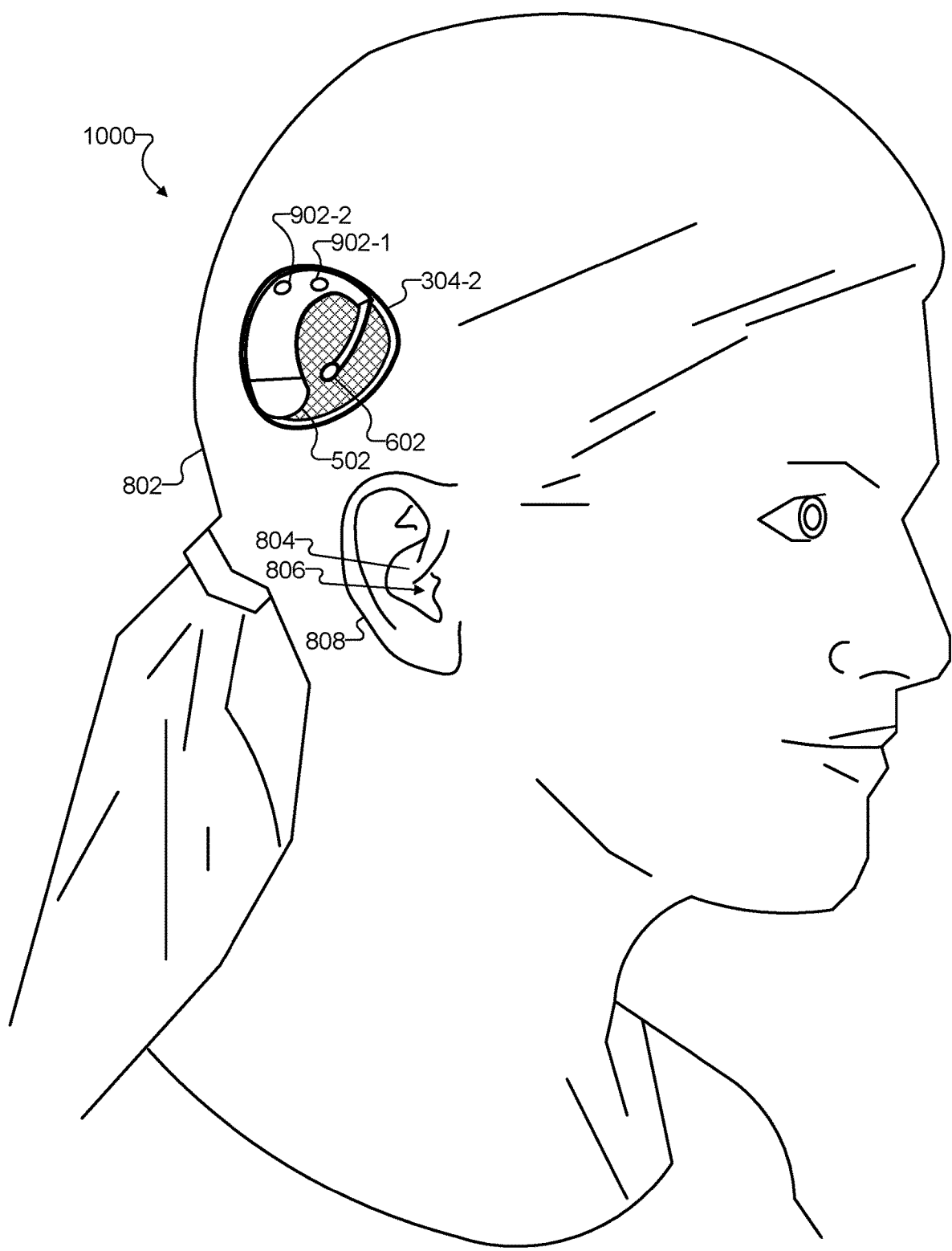
FIG. 10 illustrates an additional exemplary operational configuration of the cochlear implant system of FIG. 5 while being worn by a recipient according to principles described herein.

To illustrate cochlear implant system 500 when operating in the second mode, FIG. 10 depicts an additional exemplary operational configuration 1000 of cochlear implant system 500 being worn by recipient 802. As shown, the same elements described above in relation to operational configuration 800 are shown in FIG. 10. However, rather than wearing microphone assembly 502 on the ear, recipient 802 has physically attached microphone assembly 502 to the implementation of OTE sound processor 304 being used (i.e., OTE sound processor 304-2 in this example). Recipient 802 may thus modularly move microphone assembly 502 between her ear and her OTE sound processor as desired (e.g., moving it to the ear to answer a call, moving it back to the OTE sound processor when engaging in sports or taking a shower, etc.).

Figure 11:
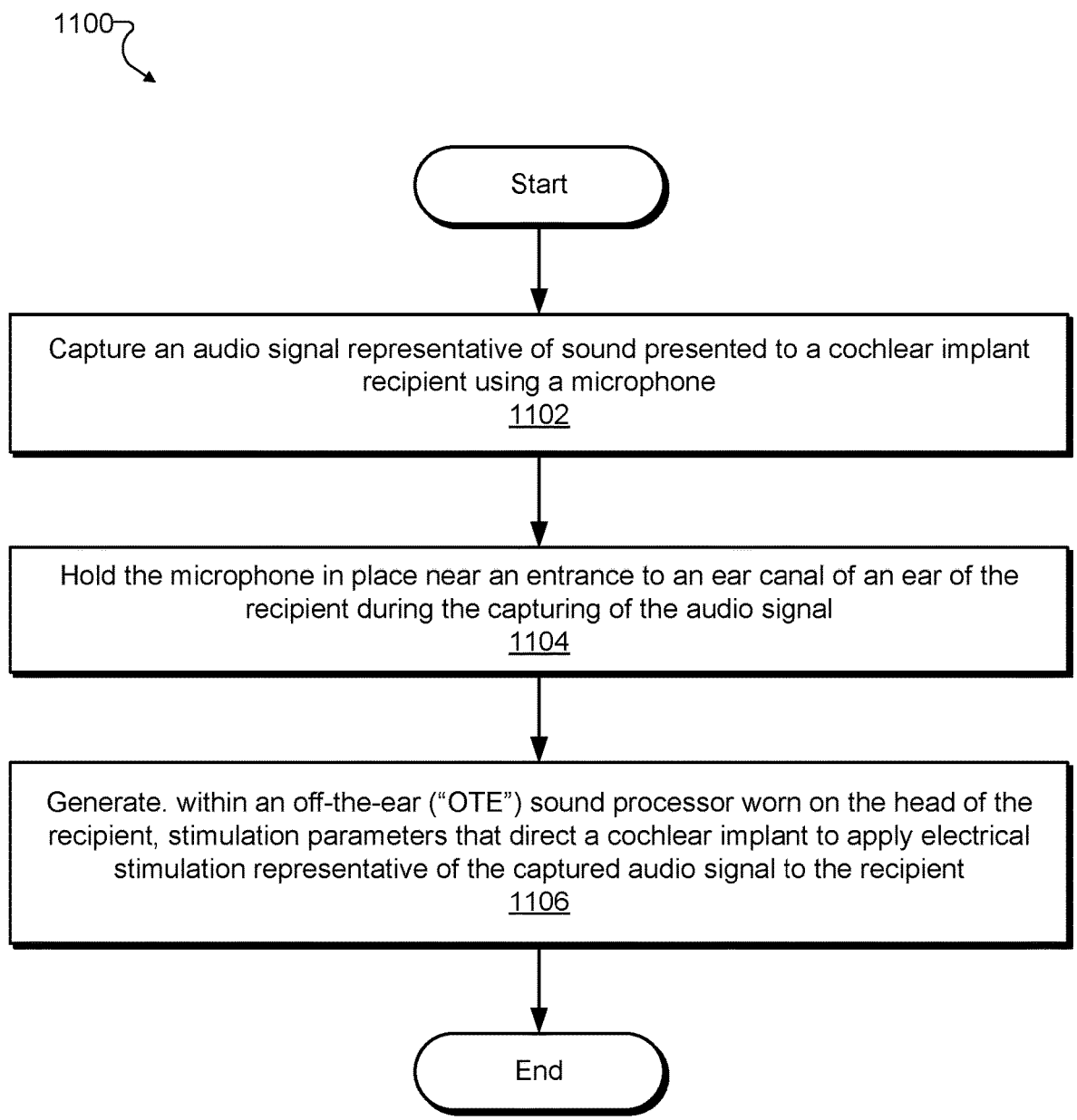
FIG. 11 illustrates an exemplary method employing microphones near the ear with OTE sound processors according to principles described herein.

FIG. 11 illustrates an exemplary cochlear implant method 1100 for employing a microphone near the ear with an OTE sound processor. One or more of the operations shown in FIG. 11 may be performed by cochlear implant system 500 (e.g., by various components included within cochlear implant system 500) and/or by any implementation thereof. While FIG. 11 illustrates exemplary operations according to one embodiment, other embodiments may omit, add to, reorder, and/or modify any of the operations shown in FIG. 11.

In operation 1102, a microphone included within a cochlear implant system used by a recipient may capture an audio signal representative of sound presented to the recipient. Operation 1102 may be performed in any of the ways described herein.

In operation 1104, a retention device included within the cochlear implant system may hold the microphone in place near an entrance to an ear canal of an ear of the recipient. For instance, the retention device may hold the microphone in place during the capturing of the audio signal performed in operation 1102. In some examples, the retention device may be assembled together with the microphone in a microphone assembly included within the cochlear implant system. Operation 1104 may be performed in any of the ways described herein.

In operation 1106, electronic circuitry included within the cochlear implant system may generate stimulation parameters that, when transmitted to a cochlear implant implanted within the recipient, direct the cochlear implant to apply electrical stimulation representative of the captured audio signal to the recipient. In some examples, the electronic circuitry may be included within a housing of an OTE sound processor included within the cochlear implant system and communicatively coupled with the microphone assembly. The housing of the OTE sound processor may be configured to be worn, during the capturing of the audio signal of operation 1102 and the holding in place of the microphone near the entrance to the ear canal of operation 1104, on a head of the recipient at a location that is off the ear of the recipient.

Operation 1106 may be performed in any of the ways described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A cochlear implant system for use by a recipient, the cochlear implant system comprising:
   a microphone assembly including
      a microphone configured to capture an audio signal representative of sound presented to the recipient, and
      a retention device configured to hold the microphone in place near an entrance to an ear canal of an ear of the recipient; and
   an off-the-ear (OTE) sound processor communicatively coupled with the microphone assembly and including
      a housing configured to be worn on a head of the recipient at a location that is off the ear of the recipient, the housing further configured to physically attach to the microphone assembly so as to allow the microphone assembly to be worn at the location that is off the ear when the microphone assembly is not being worn at the ear using the retention device, and
      electronic circuitry included within the housing and configured to generate stimulation parameters that, when transmitted to a cochlear implant implanted within the recipient, direct the cochlear implant to apply electrical stimulation representative of the captured audio signal to the recipient.

2. The cochlear implant system of claim 1, wherein:
the location off the ear of the recipient at which the housing of the OTE sound processor is configured to be worn is an implantation site of the cochlear implant; and
the OTE sound processor further includes, within the housing, an antenna configured to transcutaneously transmit the stimulation parameters from the electronic circuitry to the cochlear implant.

3. The cochlear implant system of claim 1, wherein the retention device configured to hold the microphone in place near the entrance to the ear canal of the ear is implemented by an ear hook.

4. The cochlear implant system of claim 1, wherein the retention device configured to hold the microphone in place near the entrance to the ear canal of the ear is implemented by an earmold.

5. The cochlear implant system of claim 1, wherein:
the cochlear implant system further includes a cable configured to electrically connect the microphone of the microphone assembly to the electronic circuitry of the OTE sound processor; and
the OTE sound processor is communicatively coupled with the microphone assembly by way of a wired interface implemented by the cable.

6. The cochlear implant system of claim 1, wherein:
the microphone assembly further includes
a wireless transmitter configured to wirelessly transmit the captured audio signal to the electronic circuitry of the OTE sound processor, and
a power supply for powering the wireless transmitter; and
the OTE sound processor is communicatively coupled with the microphone assembly by way of a wireless interface implemented by the wireless transmitter.

7. The cochlear implant system of claim 1, wherein:
the retention device configured to hold the microphone in place near the entrance to the ear canal of the ear is implemented by an ear hook;
the microphone assembly further includes
a plurality of additional microphones integrated into the ear hook, and
front-end processing circuitry integrated into the ear hook and configured to generate a combined audio signal based on a combination of additional audio signals captured by the plurality of additional microphones to represent the sound presented to the recipient; and
the electronic circuitry is configured to generate the stimulation parameters when operating in a first mode, and is further configured, when operating in a second mode, to generate additional stimulation parameters that, when transmitted to the cochlear implant, direct the cochlear implant to apply electrical stimulation representative of the combined audio signal to the recipient.

8. The cochlear implant system of claim 1, wherein:
the OTE sound processor further includes
a plurality of additional microphones included within the housing, and
front-end processing circuitry included within the housing and configured to generate a combined audio signal based on a combination of additional audio signals captured by the plurality of additional microphones to represent the sound presented to the recipient; and
the electronic circuitry is configured to generate the stimulation parameters when operating in a first mode, and is further configured, when operating in a second mode, to generate additional stimulation parameters that, when transmitted to the cochlear implant, direct the cochlear implant to apply electrical stimulation representative of the combined audio signal to the recipient.

9. The cochlear implant system of claim 1, wherein:
the electronic circuitry is configured to operate in either a first mode or a second mode;
the electronic circuitry is configured to operate in the first mode when the microphone assembly is being worn at the ear using the retention device; and
the electronic circuitry is configured to operate in the second mode when the microphone assembly is physically attached to the housing so that the microphone assembly is worn at the location that is off the ear.

10. The cochlear implant system of claim 9, wherein:
the OTE sound processor further includes an additional microphone within the housing, the additional microphone configured to capture an additional audio signal representative of the sound presented to the recipient;
the electronic circuitry is configured to
generate the stimulation parameters that direct the cochlear implant to apply the electrical stimulation representative of the captured audio signal when operating in the first mode, and
generate stimulation parameters that, when transmitted to the cochlear implant, direct the cochlear implant to apply electrical stimulation representative of the additional audio signal when operating in the second mode.

11. The cochlear implant system of claim 9, wherein:
the OTE sound processor does not include any microphone;
the microphone assembly further includes an additional microphone configured to capture an additional audio signal representative of the sound presented to the recipient;
the electronic circuitry is configured to
generate the stimulation parameters that direct the cochlear implant to apply the electrical stimulation representative of the captured audio signal when operating in the first mode, and
generate stimulation parameters that, when transmitted to the cochlear implant, direct the cochlear implant to apply electrical stimulation representative of the additional audio signal when operating in the second mode.

12. The cochlear implant system of claim 1, further comprising a contralateral microphone assembly including
a contralateral microphone configured to capture a contralateral audio signal representative of the sound presented to the recipient; and
a contralateral retention device configured to hold the contralateral microphone in place near an entrance to an ear canal of an opposite ear of the recipient contralateral to the ear of the recipient;
wherein the OTE sound processor is further communicatively coupled with the contralateral microphone assembly and the electronic circuitry is configured to generate the stimulation parameters to direct the cochlear implant to apply electrical stimulation that is further representative of the captured contralateral audio signal to the recipient.

13. A cochlear implant system for use by a recipient, the cochlear implant system comprising:
a microphone assembly including
a first microphone configured to capture a first audio signal representative of sound presented to the recipient,
an ear hook configured to hold the first microphone in place near an entrance to an ear canal of an ear of the recipient,
a second microphone and a third microphone integrated into the ear hook and configured to capture, respectively, a second audio signal and a third audio signal representative of the sound presented to the recipient, and
front-end processing circuitry integrated into the ear hook and configured to generate a combined audio signal based on a combination of the second and third audio signals; and
an off-the-ear (OTE) sound processor communicatively coupled with the microphone assembly and including
a housing configured to be worn on a head of the recipient at a location that is off the ear of the recipient, the housing further configured to physically attach to the microphone assembly so as to allow the microphone assembly to be worn at the location that is off the ear when the microphone assembly is not being worn at the ear using the ear hook, and
electronic circuitry included within the housing and configured to operate in either
a first mode in which the electronic circuitry generates stimulation parameters that, when transmitted to a cochlear implant implanted within the recipient, direct the cochlear implant to apply electrical stimulation representative of the first audio signal to the recipient, or
a second mode in which the electronic circuitry generates stimulation parameters that, when transmitted to the cochlear implant, direct the cochlear implant to apply electrical stimulation representative of the combined audio signal to the recipient;
wherein:
the electronic circuitry is configured to operate in the first mode when the microphone assembly is being worn at the ear using the ear hook; and
the electronic circuitry is configured to operate in the second mode when the microphone assembly is physically attached to the housing so that the microphone assembly is worn at the location that is off the ear.

14. The cochlear implant system of claim 13, wherein:
the location off the ear of the recipient at which the housing of the OTE sound processor is configured to be worn is an implantation site of the cochlear implant; and
the OTE sound processor further includes, within the housing, an antenna configured to transcutaneously transmit the stimulation parameters from the electronic circuitry to the cochlear implant.

15. The cochlear implant system of claim 13, wherein:
the cochlear implant system further includes a cable configured to electrically connect the first microphone of the microphone assembly to the electronic circuitry of the OTE sound processor; and
the OTE sound processor is communicatively coupled with the microphone assembly by way of a wired interface implemented by the cable.

16. The cochlear implant system of claim 13, wherein:
the microphone assembly further includes
a wireless transmitter configured to wirelessly transmit the first audio signal to the electronic circuitry of the OTE sound processor, and
a power supply for powering the wireless transmitter; and
the OTE sound processor is communicatively coupled with the microphone assembly by way of a wireless interface implemented by the wireless transmitter.

17. A method comprising:
capturing, by a microphone included within a cochlear implant system used by a recipient, an audio signal representative of sound presented to the recipient;
holding in place, by a retention device assembled together with the microphone in a microphone assembly, the microphone near an entrance to an ear canal of an ear of the recipient during the capturing of the audio signal; and
generating, by electronic circuitry included within a housing of an off-the-ear (OTE) sound processor included within the cochlear implant system and communicatively coupled with the microphone assembly, stimulation parameters that, when transmitted to a cochlear implant implanted within the recipient, direct the cochlear implant to apply electrical stimulation representative of the captured audio signal to the recipient;
wherein the housing of the OTE sound processor is configured to be worn, during the capturing of the audio signal and the holding in place of the microphone near the entrance to the ear canal, on a head of the recipient at a location that is off the ear of the recipient, and
wherein the housing is further configured to physically attach to the microphone assembly so as to allow the microphone assembly to be worn at the location that is off the ear when the microphone assembly is not being worn at the ear using the retention device.

18. The method of claim 17, further comprising transcutaneously transmitting, by an antenna included within the housing of the OTE sound processor, the stimulation parameters from the electronic circuitry to the cochlear implant;
wherein the location off the ear of the recipient at which the housing of the OTE sound processor is configured to be worn is an implantation site of the cochlear implant.

19. The method of claim 17, wherein the holding in place of the microphone near the entrance to the ear canal is performed by an ear hook implementing the retention device.

20. The method of claim 17, wherein the holding in place of the microphone near the entrance to the ear canal is performed by an earmold implementing the retention device.

* * * * *